United States Patent [19]

Erskine

[11] Patent Number: 5,797,880
[45] Date of Patent: Aug. 25, 1998

[54] CATHETER AND PLACEMENT NEEDLE ASSEMBLY WITH RETRACTABLE NEEDLE

[75] Inventor: Timothy J. Erskine, Sandy, Utah

[73] Assignee: Becton and Dickinson and Company, Franklin Lakes, N.J.

[21] Appl. No.: 706,578

[22] Filed: Sep. 5, 1996

[51] Int. Cl.$^6$ ..................................................... A61M 5/00
[52] U.S. Cl. ........................ 604/110; 604/198; 604/168; 604/162
[58] Field of Search ..................... 604/110, 198, 604/162, 263, 168, 167, 169

[56] References Cited

U.S. PATENT DOCUMENTS

| | | | |
|---|---|---|---|
| 4,108,175 | 8/1978 | Orton | 604/168 |
| 4,207,870 | 6/1980 | Eldridge | 604/168 |
| 4,307,731 | 12/1981 | Kaufman | 128/766 |
| 4,512,766 | 4/1985 | Vailancourt | 604/169 |
| 4,747,831 | 5/1988 | Kulli | 604/110 |
| 4,917,671 | 4/1990 | Chang | 604/168 |
| 5,125,414 | 6/1992 | Dysarz | 128/763 |
| 5,129,884 | 7/1992 | Dysarz | 604/164 |
| 5,501,675 | 3/1996 | Erskine | 604/263 |
| 5,573,510 | 11/1996 | Isaacson | 604/158 |
| 5,575,777 | 11/1996 | Cover | 604/110 X |

Primary Examiner—Sam Rimell
Assistant Examiner—Luke J. Yeh
Attorney, Agent, or Firm—Eric M. Lee

[57] ABSTRACT

A catheter and needle assembly includes a hollow handle with a longitudinal axis defining a cavity. The handle has a proximal end and a distal end that defines a wall with an inside surface and an outside surface that has an axial protuberance thereon. The protuberance having an axial opening through said wall into the cavity. The assembly also includes a catheter with a proximal end, a distal end and an open passageway therethrough. The catheter has a hub affixed to the catheter proximal end, the catheter hub being releasably mounted on the protuberance so that the catheter projects axially from the distal end of the handle. Included in the assembly is an elongate needle with an open bore therethrough with a sharp distal point and a proximal end. The needle has a first position wherein it is disposed within the cavity through the opening and into the catheter passageway so that the sharp distal point of the needle projects axially beyond the distal end of the catheter. A spring directly acts on the needle to urge the needle to a second position wherein the needle is substantially within the cavity. The assembly has a releasable latch associated with the handle to retain the needle in the first position, the latch is movable to a release position wherein the latch no longer retains the needle in said first position.

13 Claims, 7 Drawing Sheets

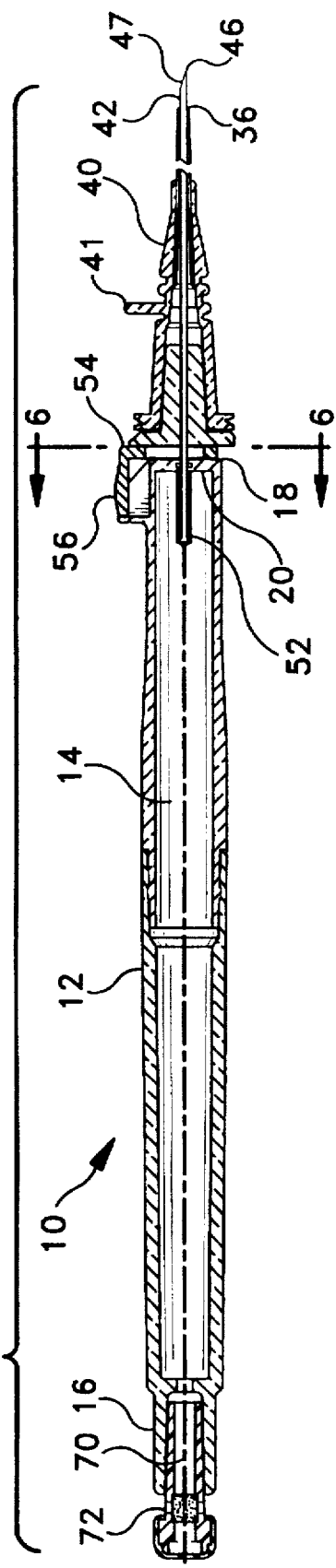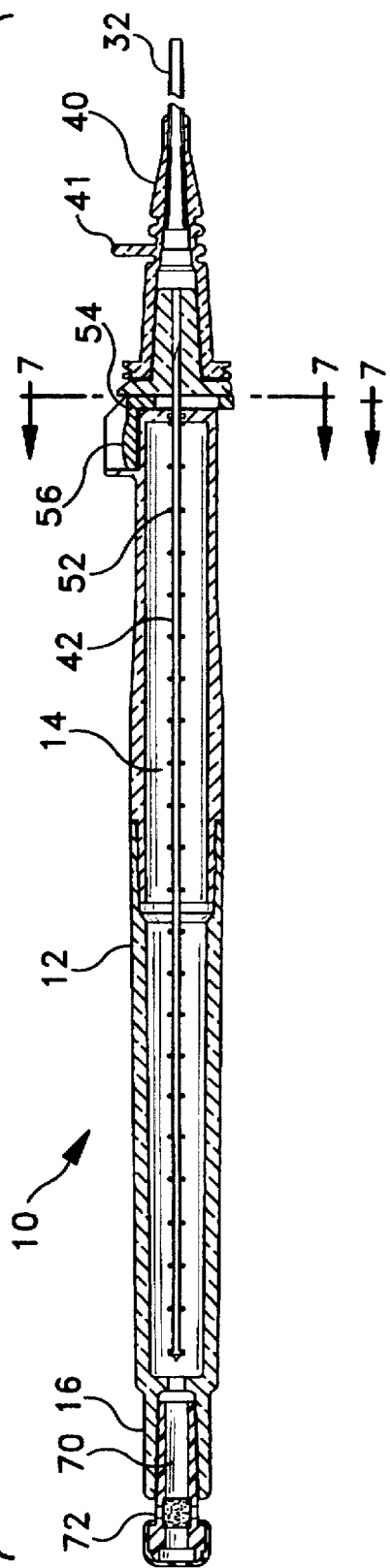

CATHETER AND PLACEMENT NEEDLE ASSEMBLY WITH RETRACTABLE NEEDLE

FIELD OF INVENTION

This invention is generally related to intravascular catheters and devices for placing a catheter and more particularly to a catheter needle placement assembly with a protected needle retraction system.

BACKGROUND

An intravascular catheter is generally a flexible small diameter tube inserted into a patient's blood vessel to allow withdrawal or addition of fluid. Typically, a practitioner places the catheter by locating a target blood vessel for the placement, then pierces the patient's skin and the blood vessel wall with an inserter needle, uses the needle to lead the catheter into the vessel and then removes the needle, leaving the catheter in the vessel. Catheters may be inserted into blood vessels either through the bore of the needle or over-the-needle. In this disclosure, catheters that are inserted over-the-needle are described. Additionally, a convention is followed in this disclosure using the term "proximal" to refer to the portion of the device closest to the practitioner and the term "distal" for the portion of the device toward the patient or away from the practitioner.

Over-the-needle catheters are generally supplied already mounted on an inserter needle in a sterile, ready-to-use, unit package. In its simplest form, the over-the-needle catheter generally resembles one tube slidably fit within another tube, the flexible catheter being outermost with a sharp beveled point inserter needle slidably fit within the catheter bore so that the sharp distal inserter needle point projects beyond a gently tapered distal end of the catheter. In placement of these over-the-needle catheters, the needle, with the catheter outside, is held by the practitioner, generally with the point bevel face up, longitudinally aligned with the target blood vessel. The needle is then inserted at a shallow angle through the patient's skin into the blood vessel. The practitioner then often determines that the needle is properly positioned within the blood vessel by allowing a small quantity of the patient's blood to flow through the hollow needle, impelled by the patient's blood pressure, so that the small quantity of blood can be seen at the rear of the needle. This practice of using the patient's blood to signal proper placement of needle within the target vessel is termed "flashing." The flashing step has the purpose of confirming that the catheter is properly inserted into the blood vessel. Once the proper placement is confirmed, the practitioner applies finger pressure to the vessel over the distal tip of the needle and the catheter to occlude further blood flow, withdraws the needle and attaches a fluid handling device to the catheter hub.

Once the inserter needle is removed, it is a "blood-contaminated sharp" and must be properly handled. With the recognition by the medical device art of the risk of transmission of Acquired Immunosuppressive Deficiency Syndrome (AIDS) by blood contaminated sharps, devices such as disclosed in U.S. Pat. No. 4,747,831 were developed. The patent discloses a cannula insertion set with safety retracting needle. The device disclosed in the patent provides a cannula insertion needle projecting from a hollow handle into which the needle is withdrawn after the placement is completed. Anyone handling the device following the withdrawal is thus substantially protected from the contaminated needle because it is contained within the inserter handle. The device includes a separate needle hub that is proximally displaced to withdraw the needle into the hollow handle.

An improvement to retractable-needle cannula insertion devices is disclosed in U.S. application Ser. No. 08/422,662. The disclosed improvement includes provisions for containing and controlling the flashing by providing a chamber within a needle hub contained in the handle that is fluidly connected to the needle to allow visualization of the blood and substantially retain the blood within the chamber when the needle is withdrawn into the handle and the device is in the disposal process.

All of the devices referred to above enable practitioners to place a catheter into a patient's blood vessel, then withdraw the needle into a protected location to substantially eliminate the possibility of needle sticks with the used needle. All of these disclosed devices have more parts than the simple non-retractable needle devices commonly used. Thus, the disclosed devices require more complex assembly and are more expensive than the simple non-retractable devices. If a retractable needle device were available that had fewer parts, thus being more efficient to assemble and potentially less expensive, the art of placing catheters would be advanced. Such a device is disclosed below.

SUMMARY

A catheter and needle assembly of the present invention includes a hollow handle with a longitudinal axis defining a cavity. The handle has a proximal end and a distal end, with the distal end defining a wall with an inside surface and an outside surface. The outside surface has an axial protuberance thereon, and an axial opening through the wall into the cavity. The assembly also includes a catheter with a proximal end, a distal end and an open passageway therethrough. The catheter has a hub affixed to the catheter proximal end, the catheter hub is releasably mounted on the protuberance so that the catheter projects axially from the distal end of the handle. The assembly also has an elongate needle with an open bore therethrough with a sharp distal point and a proximal end. The needle has a first position where the needle is disposed within the cavity and through the opening into the catheter passageway so that the sharp distal point of the needle projects axially beyond the distal end of the catheter. There is a spring cooperating with the needle to urge the needle to a second position wherein the needle is substantially within the cavity. The assembly also has a releasable latch associated with the handle to retain the needle in the first position. The latch is movable to a release position wherein the latch no longer retains the needle in the first position.

The catheter and needle assembly of the invention is simple to manufacture, and has fewer parts than the cited available retractable needle assemblies. The assembly of the invention is intuitive for a practitioner to use to place the catheter and to withdraw the needle into the handle for disposal.

BRIEF DESCRIPTION OF THE DRAWINGS

FIG. 3 is a cross-sectional view of the invention of FIG. 1 taken along the line 3—3;

FIG. 4 is a cross-sectional view, analogous to FIG. 3, with the needle retracted;

DETAILED DESCRIPTION

Figure 1:
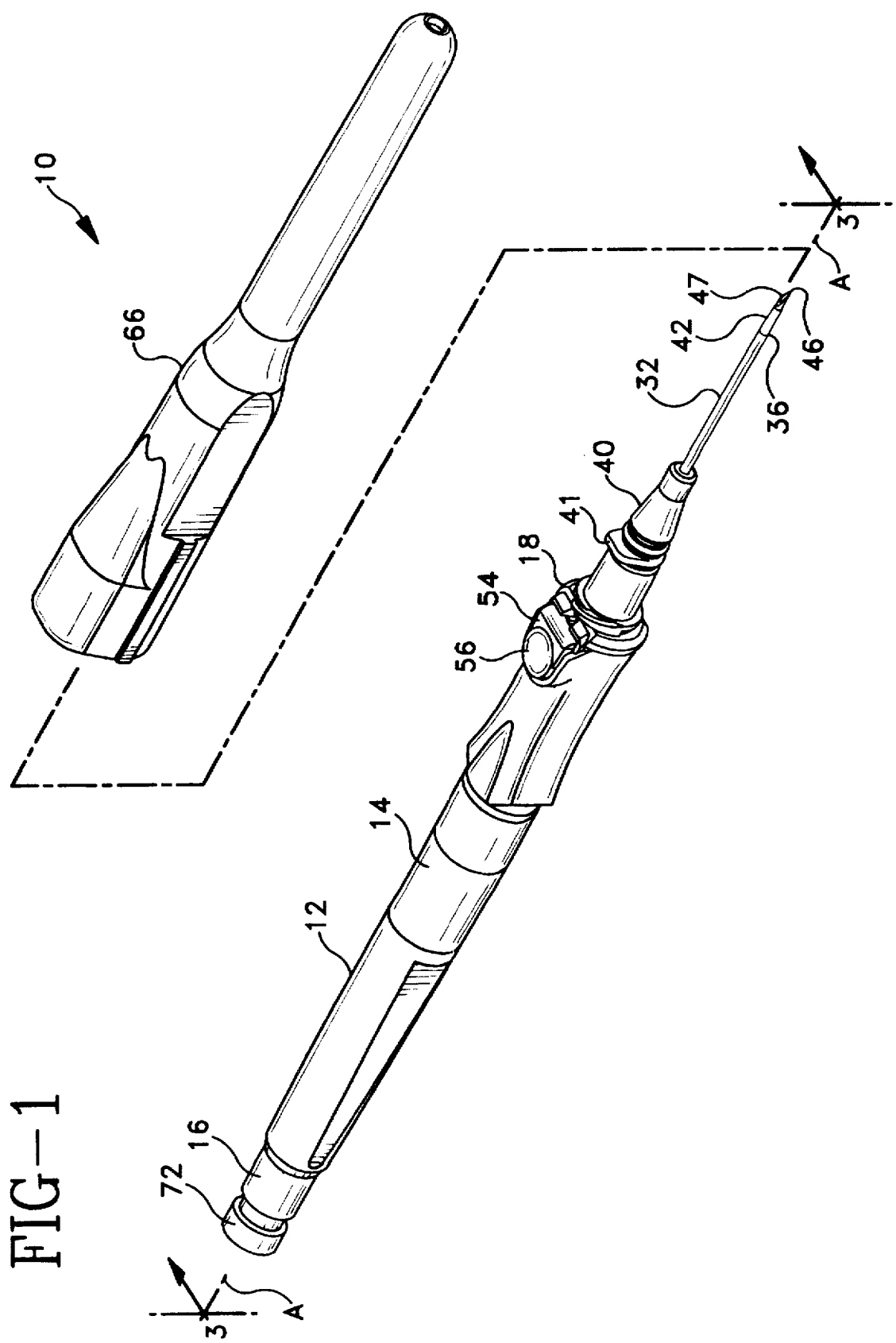
FIG. 1 is a partially exploded perspective view of the preferred catheter placement device of the present invention.
Figure 2:
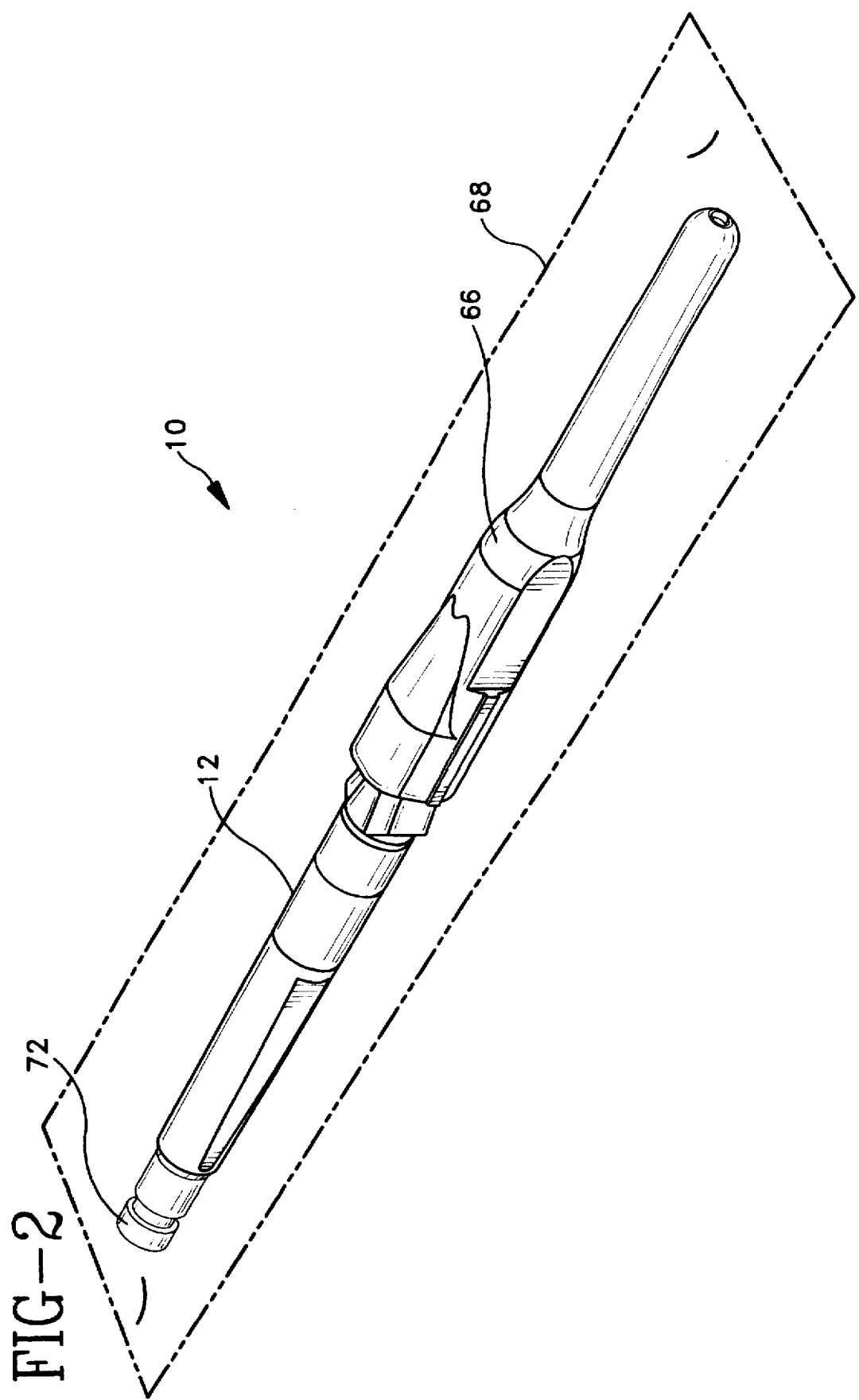
FIG. 2 illustrates the invention of FIG. 1 assembled and placed in a package.

While this invention is satisfied by embodiments in many different forms, there are shown in the drawings and herein described in detail, preferred embodiments of the invention with the understanding that the present disclosure is to be considered exemplary of the principles of the invention and is not considered to limit the invention to the embodiment illustrated. The scope of the invention is measured by the appended claims and their equivalents.

Referring to FIGS. 1 to 7, a preferred catheter and needle assembly 10 of the present invention includes a hollow handle 12 with a longitudinal axis "A" defining an elongate cavity 14. Handle 12 has a proximal end 16 and a distal end 18. Preferably, proximal end 16 includes an axial opening 70 that includes a vent 72. Vent 72 preferably selectively allows air transmission into and out of cavity 14 and substantially prevents fluid flow into or out of cavity 14. Distal end 18 defines a wall 20 with an inside surface 22 and an outside surface 24 having an axial protuberance 26 thereon. Protuberance 26 has an axial opening 30 through wall 20 into cavity 14. Assembly 10 includes a catheter 32 that has a proximal end 34, a distal end 36 and an open passageway 38 therethrough. Catheter 32 has a catheter hub 40 affixed to catheter proximal end 34, that is releasably mounted on protuberance 26 so that catheter 32 projects axially from the distal end 14 of the handle.

Preferred assembly 10 also includes an elongate needle 42 with an open bore 44 therethrough and has a sharp distal point 46. Needle 42 has a proximal end 48 having an outwardly extending flange 50. Needle 42 has a first position, best seen in FIGS. 1 and 3, with needle 42 disposed within handle 12 and through opening 30 into catheter passageway 38 so that sharp distal point 46 projects axially beyond distal end 36 of the catheter.

Figure 5:
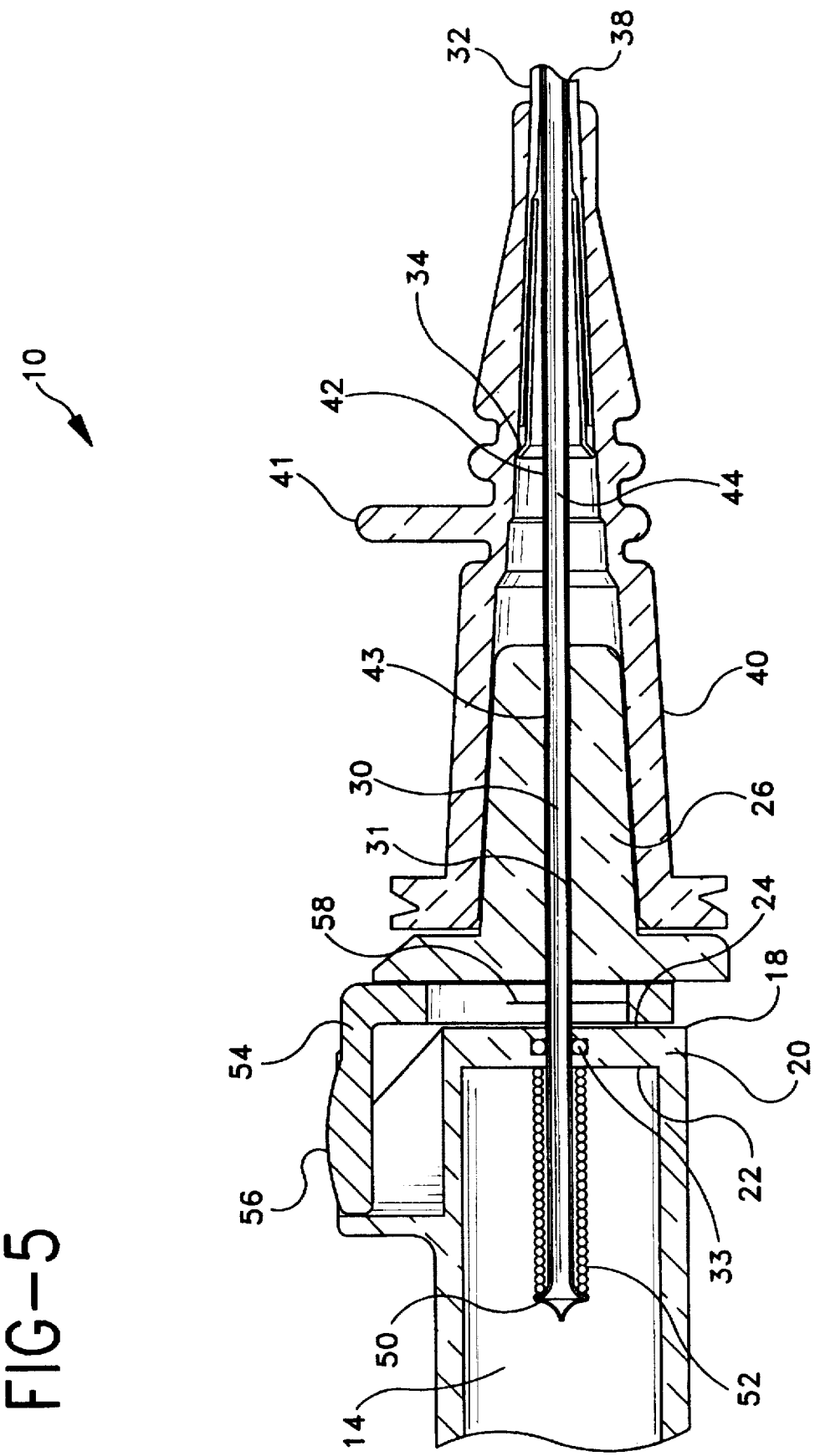
FIG. 5 is an enlargement of the hub and latch area of FIG. 3

Assembly 10 preferably has a spring 52, preferably a coil spring, directly acting on needle 42 to urge the needle to a second position, best seen in FIG. 4, where needle 42 is substantially within handle 12, spring 52 preferably being disposed coaxially about needle 42 and in compression between flange 50 and inside surface 22 of the distal end of handle 12 when needle 42 is in first position. Referring to FIG. 5, flange 50 preferably includes a one-way valve 51, that opens to allow a blood flash to enter handle 12 when needle distal point 46 enters a patient's blood vessel so that a practitioner can confirm placement of the needle in the target blood vessel. One-way valve 51 substantially prevents flow of blood present in cavity 14 out of needle bore 44 when needle 42 is moved from the first position to the second position. As shown in the Figs., valve 51 is preferably a "duckbill type" valve formed from a resilient material such as a low durometer silicone elastomer and the like, but other one-way valves such as a "trap-door" and the like are also suitable and considered within the scope of the invention.

Figure 7:
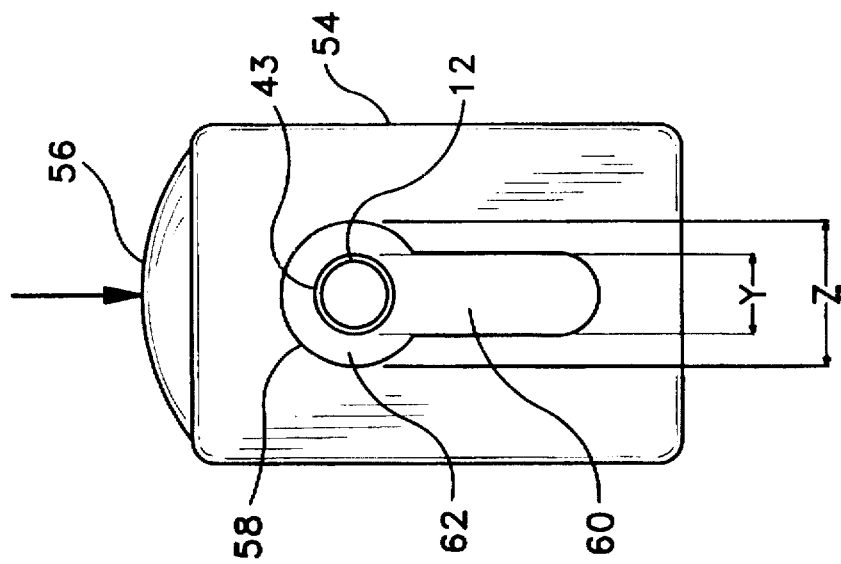
FIG. 7 is an enlarged partial cross-sectional view of the latch disengaged from the needle taken from FIG. 4 along the line 7—7.
Figure 6:
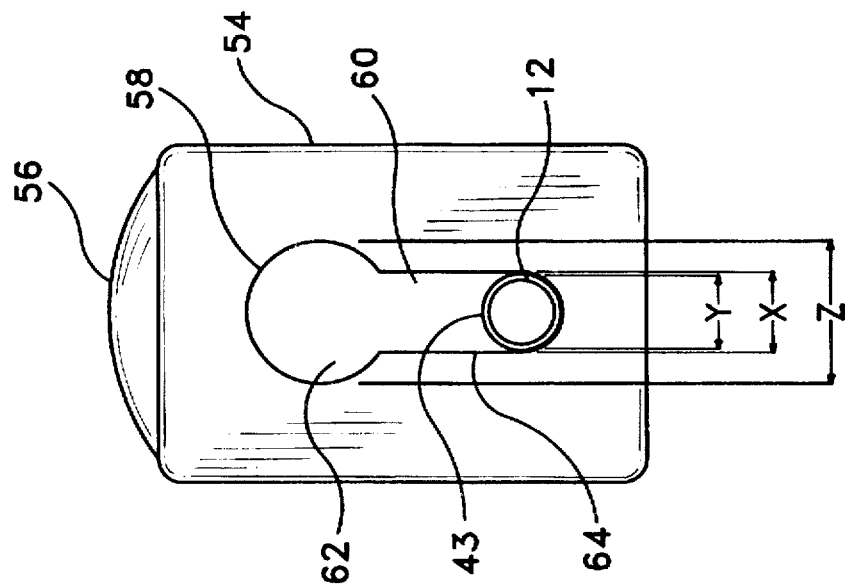
FIG. 6 is an enlarged partial cross-sectional view of the latch engaged with the needle taken from FIG. 3 along the line 6—6.

Referring to FIGS. 6 and 7, assembly 10 has a releasable latch 54 associated with handle 12 to retain needle 42 in the first position, as seen in FIGS. 1, 3, 5 and 6. Latch 54 is movable to a release position, best seen in FIG. 7, wherein latch 54 no longer retains needle 42 in first position. Latch 54 preferably has a trigger 56 located distally on handle 12 to selectively move latch 54 with respect to needle 42 from the latch position to the release position.

In preferred needle assembly 10 latch 54 includes an elongate slot 58 that has a latching region 60 with a width "x" less than an outside diameter "y" of needle 42 and a release region 62 with a width "z" greater than outside diameter "x" of needle 42. Latch 54 is disposed about and substantially normal to the axis of needle 42 so that the needle is positioned in slot 58 and interferes with latch 54 in latching region 60 to retain needle 42 is in the first position. Latch 54 is movable with respect to needle 42 so that the needle is positioned in release region 62 and substantially does not contact latch 54, thereby allowing spring 52 to urge needle 42 to the second position. Preferably, latching region 60 of latch 54 includes a sharpened edge 64 for engaging and releasably retaining needle 42 in the first position.

Opening 30 in distal end wall 20 preferably forms a substantially fluid resistant seal 31 with an outside surface 43 of needle 42. Fluid tight seal 31 may be formed by careful matching of the size of opening 30 to the outside diameter "x" of needle 42. Preferably, fluid resistant seal 31 is formed by including a resilient gasket 33 at opening 30. Resilient gasket 33 may be an "O" ring as shown in FIG. 5, or a layer of resilient material and the like that forms a substantially fluid tight seal with surface 43 of the needle.

Referring again to FIGS. 1 and 2, assembly 10 is preferably supplied with a shield 66, sized and shaped to fit onto hollow handle 12 to obstruct inadvertent access to needle 42 and trigger 56 for releasing latch 54. Preferably, assembly 10 with shield 66 positioned thereon is placed within a sealed package 68, as indicated in phantom in FIG. 2, that is formed from materials substantially resistant to the passage of microorganisms. The sealed package is then preferably exposed to conditions sufficient to render any microorganisms within the package substantially non-viable. Suitable package materials include, but are not limited to, paper, thermoplastic film, non-woven materials, combinations thereof and the like. Suitable conditions for rendering microorganisms non-viable include, but are not limited to, chemical sterilants such as ethylene oxide, hydrogen peroxide vapor and the like; and exposure to ionizing radiation such as gamma radiation, beta particles and the like. The packaged assembly is then considered to be sterile until the package is opened. When materials are selected for forming assembly 10 and package 68, there should be consideration of the particular materials' compatibility with the planned sterilization conditions.

Suitable materials for forming hollow handle 12 and catheter hub 40 include, but are not limited to, thermoplastic polymeric resins such as polycarbonate, polystyrene, polypropylene and the like. Handle 12 is preferably formed from a substantially transparent material. Suitable materials for forming catheter 32 include thermoplastic resins such as polytetrafluoroethylene (PTFE), polyurethane and the like.

Preferably, catheter 32 is formed from a thermoplastic hydrophilic polyurethane that softens with exposure to physiological conditions present in the patient's body. Needle 42 and coil spring 52 are preferably formed from a stainless steel alloy or the like. Latch 54 and trigger 56 preferably are formed as a unitary structure from a stainless steel alloy or the like. Catheter hub 40 preferably includes an outwardly extending tab 41 that is preferably substantially longitudinally aligned with a bevel surface 47 of sharp distal point 46 and with trigger 56 of latch 54. Tab 41 is useful for advancing catheter 32 over needle 42 into the patient's blood vessel when the needle is being withdrawn after placement of the needle in the patient's blood vessel.

A preferred method for a practitioner to place a catheter into a patient's target blood includes opening package 68, removing the shielded assembly 10, then dismounting shield 66 and exposing catheter 32 with projecting needle point 46. The method includes positioning assembly 10 substantially longitudinally aligned with the target blood vessel with bevel 47 facing substantially away from the skin surface and inserting needle 42 at a shallow angle, preferably less than about 35 degrees, into the skin, so that needle point 46 enters the target blood vessel. The practitioner then preferably observes a blood flashback in cavity 14.

After confirming placement of needle 42 in the target blood vessel, the method includes the practitioner advancing catheter 32 distally axially along needle 42 into position in the blood vessel, preferably using upwardly extending tab 41. As placement of catheter 12 is achieved, the method includes the practitioner placing a finger from his other hand on the patient's skin over the blood vessel approximately over distal end 36 of the catheter. By placing his finger on the patient's skin and applying sufficient pressure on the skin, the practitioner thereby substantially occludes blood flow through the catheter. The method then includes the practitioner withdrawing the needle from bore 14 of the catheter by depressing trigger 56 and releasing latch 54 so that spring 52 urges needle 42 into the proximal position within hollow handle 12. The practitioner may then attach any desired fluid handling device to catheter hub 20 and commence the planned treatment. Hollow handle 12 with needle 42 substantially within it may then be disposed of according to the facility's disposal protocol.

Preferably, when assembly 10 is manufactured, needle 42 is rotationally oriented in the hollow handle and engaged with latch 54 so beveled surface 47 is substantially aligned with trigger 56. When the assembly is unshielded in preparation for usage by the practitioner, the alignment of the needle bevel and trigger substantially directs the practitioner's grasp of the hollow handle to an intuitively proper position for insertion into the patient with needle point bevel surface 47 facing upward. Following insertion of the needle the practitioner is readily able to confirm the proper placement in the patient's blood vessel by observation of the blood flashback in cavity 14.

Figure 8:
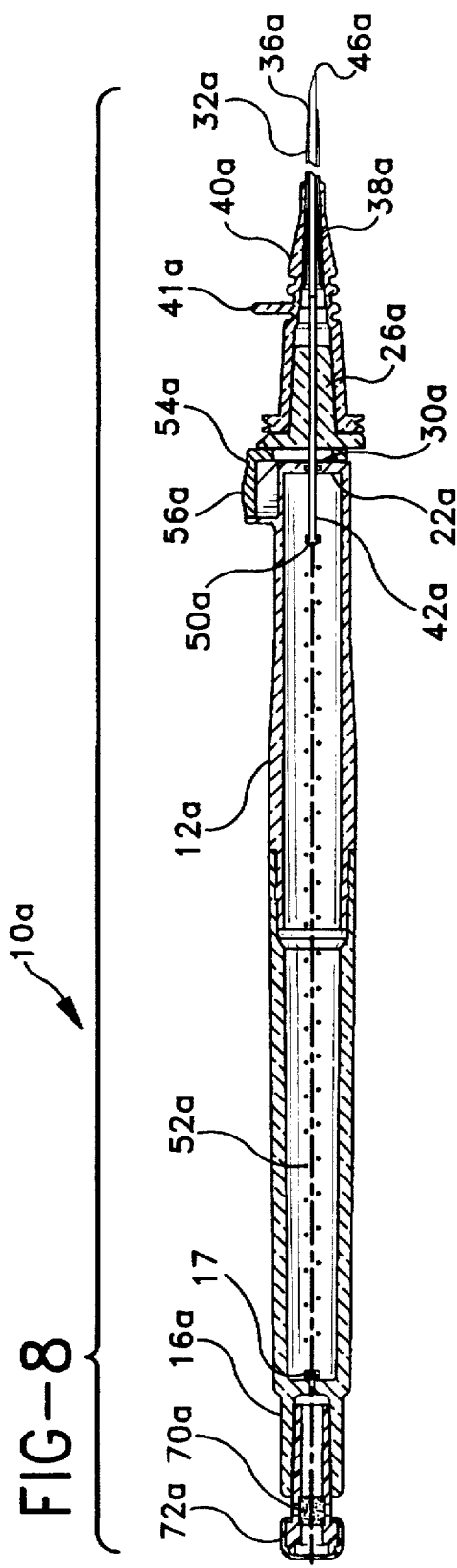
FIG. 8 is a cross-sectional view, analogous to the view of FIG. 3, of another embodiment of the invention.
Figure 9:
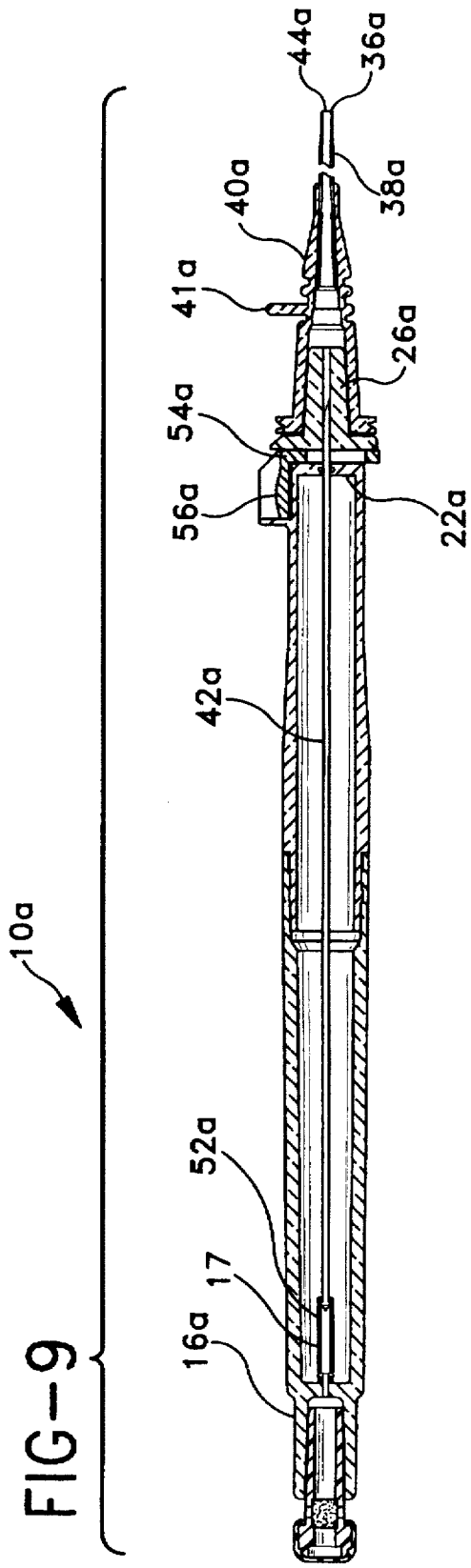
FIG. 9 is a cross-sectional view, analogous to the view of FIG. 4, of the embodiment of FIG. 8 with the needle retracted.
Figure 10:
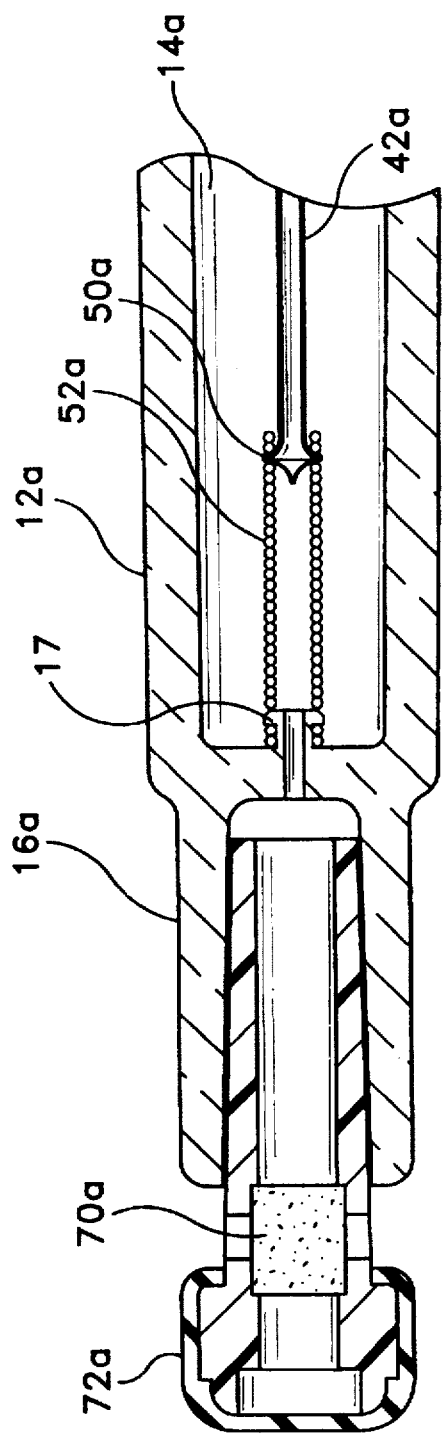
FIG. 10 is an enlargement of the distal end of the handle and needle from the view of FIG. 9, with the needle retracted.

Referring to FIGS. 8, 9 and 10, an alternate embodiment of the catheter and needle assembly of the invention is illustrated. In this embodiment there are elements similar in structure and function to the catheter and needle assembly of FIG. 1–7. Accordingly, substantially similar components that perform substantially similar functions are numbered identically to those of FIGS. 1–7 except that the suffix "a" is used to identify those components in FIGS. 8–10.

In this embodiment, catheter and needle assembly 10a includes hollow handle 12a with longitudinal axis "A" defining cavity 14a. Handle 12a has proximal end 16a and distal end 18a. Distal end 18 defines wall 20a with inside surface 22a and outside surface 24a having axial protuberance 26a thereon. Protuberance 26a has axial opening 30a through wall 20a into cavity 14a. Assembly 10a includes catheter 32a that has proximal end 34a, distal end 36a and open passageway 38a therethrough. Catheter 32a has catheter hub 40a affixed to catheter proximal end 34a, that is releasably mounted on protuberance 26a so that catheter 32a projects axially from the distal end 14a of the handle.

Assembly 10a also includes elongate needle 42a with open bore 44a therethrough and has sharp distal point 46a. Needle 42a has proximal end 48a having outwardly extending flange 50a. Needle 42a has a first position, best seen in FIG. 8, with needle 42a disposed within handle 12a and through opening 30a into catheter passageway 38a so that sharp distal point 46a projects axially beyond distal end 36a of the catheter.

Assembly 10a preferably has coil spring 52a cooperating with needle 42a to urge the needle to a second position, best seen in FIGS. 9 and 10, where needle 42a is substantially within handle 12a, spring 52a is disposed between proximal end 16a of handle 12a and flange 52 and in tension between flange 50a and an attachment 17 at proximal end 16a of handle 12a when needle 42a is in first position. Attachment 17 may be a hollow mushroom shaped flange as is shown in FIGS. 8, 9 and 10, or alternatively, spring 52a may be attached to proximal end 16a by a hot melt adhesive, snap ring or other mechanical attachments and the like. In this embodiment, assembly 10a has releasable latch 54a associated with handle 12a to retain needle 42a in the first position. Latch 54a is movable to a release position, best seen in FIG. 9, wherein latch 54a no longer retains needle 42a in first position. Latch 54a preferably has trigger 56a located distally on handle 12a to selectively move latch 54a with respect to needle 42a from the latch position to the release position.

The catheter needle assembly of the invention has fewer parts than most other available retractable catheter needle assemblies. Additionally, during manufacturing, since needle 42 does not have a separate hub, alignment of needle bevel surface 47 with trigger 56 and tab 41 is possible by simply rotating needle 42 in opening 30 and rotating catheter hub 40 about protuberance 26 until the trigger, bevel surface and tab are longitudinally aligned. The catheter needle assembly of the invention provides the practitioner with a larger available volume than most prior devices for observing flashback by utilizing the cavity to receive the flash. The assembly of the invention is intuitive for a practitioner to use, performs all of the functions of the other devices in a efficient manner and thus provides an advance to the art of vascular catheter placement.

What is claimed is:

1. A catheter and needle assembly comprising:

a hollow handle with a longitudinal axis defining a cavity, said handle having a proximal end and a distal end;

a catheter having a proximal end, a distal end and an open passageway therethrough;

a catheter hub affixed to the catheter proximal end, said catheter hub being releasably mounted adjacent to said distal end of said hollow handle so that said catheter projects axially from said distal end of said handle;

an elongate needle with an open bore therethrough with a sharp distal point and a proximal end, said needle having a first position wherein said needle is disposed within said handle and through said opening into said catheter passageway so that said sharp distal point of said needle projects axially beyond said distal end of said catheter;

a spring associated with said needle to urge said needle to a second position wherein said needle is substantially within said cavity;

a releasable latch associated with said handle to retain said needle in said first position, said latch movable to a release position wherein said latch no longer retains said needle in said first position; and a one-way valve mounted on said proximal end of said needle for relative movement with respect to said hollow handle to allow fluid flow into said cavity from said needle bore and to substantially prevent fluid flow from said cavity into said needle bore.

2. The catheter and needle assembly of claim 1 wherein said proximal end of said needle comprises an outwardly extending flange and wherein said spring is a coil spring coaxially about said needle, said spring in compression between said flange and said inside surface of said wall of said cavity when said needle is in said first position.

3. The catheter and needle assembly of claim 1 wherein said proximal end of said needle comprises an outwardly extending flange and wherein said spring is a coil spring, said spring being in tension between said flange and a wall defining a proximal end of said cavity when said needle is in said first position.

4. The catheter and needle assembly of claim 3 wherein said wall defining said proximal end of said cavity further includes an attachment for retaining an end of said spring at said proximal end of said cavity.

5. The catheter and needle assembly of claim 1 wherein said opening in said distal end wall comprises a substantially fluid tight seal with an outside surface of said needle.

6. The catheter and needle assembly of claim 5 wherein said substantially fluid tight seal further comprises a resilient gasket.

7. The catheter and needle assembly of claim 1 wherein said proximal end of said handle further comprises a selective vent sufficient to allow air transmission to and from said cavity and substantially resist passage of fluids to and from said cavity.

8. The catheter and needle assembly of claim 1 wherein said latch includes an elongate slot having a latching region with a width less than an outside diameter of said needle and a release region with a width greater than said outside diameter of said needle, said latch being disposed about and substantially normal to the axis of said needle so that said needle interferes with said latch in said latching region when said needle is in said first position, thereby retaining said needle in said first position, said latch being movable with respect to said needle so that said needle is in said release region and substantially does not contact with said latch, thereby allowing said spring to urge said needle to said second position.

9. The catheter and needle assembly of claim 8 wherein said latching region of said latch includes a sharpened edge for engaging and retaining said needle in said first position.

10. The catheter and needle assembly of claim 7 wherein said latch further includes a trigger located distally on said handle for selectively moving said latch with respect to said needle.

11. The catheter and needle assembly of claim 1 wherein said axial opening in said distal wall comprises an axial sleeve to substantially confine movement of said needle to axial movement.

12. The catheter and needle assembly of claim 1 wherein said catheter hub comprises a female luer fitting and said axial protuberance on said handle comprises a male luer taper for releasably mounting said catheter hub.

13. The catheter and needle assembly of claim 1 wherein said handle is formed from a material that is at least translucent so that a fluid flowing into said cavity from said bore of said needle is visible by an operator.

* * * * *